US012151015B2

(12) United States Patent
Zeng et al.

(10) Patent No.: US 12,151,015 B2
(45) Date of Patent: Nov. 26, 2024

(54) COLOR COSMETIC FORMULATION

(71) Applicants: Dow Global Technologies LLC, Midland, MI (US); Rohm and Haas Company, Collegeville, PA (US); Dow Silicones Corporation, Midland, MI (US)

(72) Inventors: Fanwen Zeng, Audubon, PA (US); Tian Lan, Langhorne, PA (US); Xiaodong Lu, North Wales, PA (US); Isabelle Van Reeth, Incourt Walloon Brabant (BE); Helene Dihang, Taisnières-sur-Hon (FR); Marc Eeman, Sombreffe (BE); Inna Shulman, Langhorne, PA (US)

(73) Assignees: Dow Global Technologies LLC, Midland, MI (US); Rohm and Haas Company, Collegeville, PA (US); Dow Silicones Corporation, Midland, MI (US)

( * ) Notice: Subject to any disclaimer, the term of this patent is extended or adjusted under 35 U.S.C. 154(b) by 530 days.

(21) Appl. No.: 17/269,574

(22) PCT Filed: Oct. 1, 2019

(86) PCT No.: PCT/US2019/053944
§ 371 (c)(1),
(2) Date: Feb. 19, 2021

(87) PCT Pub. No.: WO2020/076548
PCT Pub. Date: Apr. 16, 2020

(65) Prior Publication Data
US 2021/0308035 A1     Oct. 7, 2021

Related U.S. Application Data

(60) Provisional application No. 62/744,249, filed on Oct. 11, 2018.

(51) Int. Cl.
| | |
|---|---|
| *A61K 8/891* | (2006.01) |
| *A61K 8/19* | (2006.01) |
| *A61K 8/35* | (2006.01) |
| *A61K 8/37* | (2006.01) |
| *A61K 8/40* | (2006.01) |
| *A61K 8/81* | (2006.01) |
| *A61Q 1/02* | (2006.01) |
| *A61Q 17/04* | (2006.01) |

(52) U.S. Cl.
CPC ............. *A61K 8/891* (2013.01); *A61K 8/19* (2013.01); *A61K 8/35* (2013.01); *A61K 8/37* (2013.01); *A61K 8/40* (2013.01); *A61K 8/8147* (2013.01); *A61Q 1/02* (2013.01); *A61Q 17/04* (2013.01); *A61K 2800/43* (2013.01); *A61K 2800/5422* (2013.01)

(58) Field of Classification Search
CPC . A61K 8/891; A61K 8/19; A61K 8/35; A61K 8/37; A61K 8/40; A61K 8/8147; A61K 2800/43; A61K 2800/5422; A61Q 1/02; A61Q 17/04
See application file for complete search history.

(56) References Cited

U.S. PATENT DOCUMENTS

| | | | |
|---|---|---|---|
| 2,118,566 A * | 5/1938 | De Wayne | ............... A61K 8/24 |
| | | | 510/130 |
| 3,203,919 A | 8/1965 | Brachman | |
| 3,467,634 A | 9/1969 | Moriconi et al. | |
| 4,988,788 A | 1/1991 | Takarada | |
| 4,994,538 A | 2/1991 | Lee | |
| 5,731,379 A | 3/1998 | Kennan et al. | |
| 5,840,813 A | 11/1998 | Gornowicz et al. | |
| 6,060,072 A | 5/2000 | Konik et al. | |
| 6,534,590 B1 | 3/2003 | Aso et al. | |
| 8,828,372 B2 | 11/2014 | Arnaud et al. | |
| 9,486,399 B2 | 11/2016 | Zeng et al. | |
| 2008/0003195 A1 * | 1/2008 | Arnaud | .................... A61K 8/90 |
| | | | 424/78.03 |
| 2009/0186982 A1 | 7/2009 | Minge et al. | |

(Continued)

FOREIGN PATENT DOCUMENTS

| | | |
|---|---|---|
| EP | 1095953 | 5/2001 |
| EP | 1862162 | 12/2007 |

(Continued)

OTHER PUBLICATIONS

FR2983719A1 machine translation (Year: 2013).*
Search Report from corresponding Japanese Application No. 2021-513783 dated Aug. 14, 2023.

*Primary Examiner* — Robert A Wax
*Assistant Examiner* — John W Lippert, III
(74) *Attorney, Agent, or Firm* — Thomas S. Deibert

(57) ABSTRACT

A color cosmetic formulation is provided comprising: a color ingredient and a polymer blend, comprising: a single stage polymer and a silicone-grafted vinyl copolymer; wherein the single stage polymer comprises: structural units of a monoethylenically unsaturated non-ionic monomer; structural units of a monoethylenically unsaturated carboxylic acid monomer; and structural units of a multiethylenically unsaturated monomer having at least two ethylenically unsaturated groups per molecule; and wherein the silicone-grafted vinyl copolymer, comprises: structural units of a vinyl monomer; and structural units of a carbosiloxane dendrimer of formula (I).

12 Claims, No Drawings

(56) References Cited

U.S. PATENT DOCUMENTS

| | | |
|---|---|---|
| 2013/0177758 A1 | 7/2013 | Shigetomi et al. |
| 2014/0017186 A1 | 1/2014 | Wang |
| 2015/0079013 A1 | 3/2015 | Li et al. |
| 2015/0309211 A1 | 10/2015 | Huang et al. |

FOREIGN PATENT DOCUMENTS

| | | | |
|---|---|---|---|
| EP | 2181700 | 5/2010 | |
| FR | 2983719 | 6/2013 | |
| FR | 2983719 A1 * | 6/2013 | ............. A61K 8/062 |
| WO | 2013148614 | 10/2012 | |
| WO | WO-2013148614 A2 * | 10/2013 | ........... A61K 8/8141 |
| WO | 2017167667 | 10/2017 | |

* cited by examiner

COLOR COSMETIC FORMULATION

The present invention relates to a color cosmetic formulation. In particular, the present invention relates to a color cosmetic formulation including a color ingredient and a polymer blend of a single stage polymer and a silicone-grafted vinyl copolymer.

Consumers increasingly desire color cosmetic formulations that provide long wear properties, such that the formulation might be applied once and last through the work day and beyond without the need for refreshing or touching up. Given todays active lifestyles, it is no simple task to provide such long wear color cosmetic formulations.

An approach to providing such cosmetic formulations is disclosed by Konik et al. in U.S. Pat. No. 6,060,072. In U.S. Pat. No. 6,060,072, Konik et al. disclose water proof or water resistant cosmetic compositions which comprise a styrene-ethylene-propylene copolymer in an amount of 5 to 10%, a combination of a PVP/eicosene copolymer and tricontanyl PVP copolymer in an amount of 0.1 to 50%, a $C_{8-9}$ isoparaffin, a $C_{9-12}$ aliphatic hydrocarbon, or a combination thereof, in an amount of 50 to 85%.

Notwithstanding, there remains a need for new color cosmetic formulations that provide effective wear resistance with color retention.

The present invention provides a color cosmetic formulation, comprising: a color ingredient; and a polymer blend, comprising a single stage polymer and a silicone-grafted vinyl copolymer; wherein the single stage polymer, comprises: 90 to 99.8 wt % of structural units of a monoethylenically unsaturated non-ionic monomer; 0.19 to 10 wt % of structural units of a monoethylenically unsaturated carboxylic acid monomer; and 0.01 to 2 wt % of structural units of a multiethylenically unsaturated monomer having at least two ethylenically unsaturated groups per molecule; and wherein the silicone-grafted vinyl copolymer, comprises: 25 to 95 wt %, based on weight of the silicone-grafted vinyl copolymer, of structural units of a vinyl monomer; and 5 to 75 wt %, based on weight of the silicone-grafted vinyl copolymer, of structural units of a carbosiloxane dendrimer of formula (I)

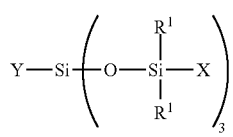

(I)

wherein each $R^1$ is independently selected from the group consisting of a $C_{1-10}$ alkyl group and an aryl group; wherein each X is a silylalkyl group of formula (II)

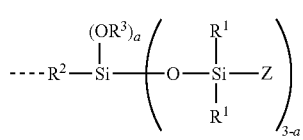

(II)

wherein $R^2$ is a $C_{2-10}$ alkylene group; wherein each $R^3$ is independently a $C_{1-10}$ alkyl group; wherein each Z is independently selected from the group consisting of a hydrogen, a $C_{1-10}$ alkyl group, an aryl group and a silylalkyl group of formula (II); wherein a is 0 to 3; wherein Y is selected from the group consisting of formula (III), (IV) and (V)

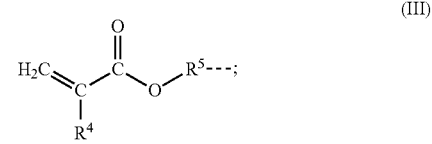

(III)

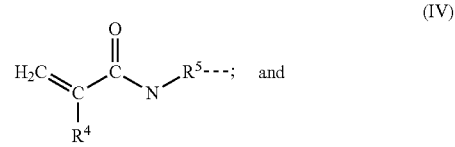

(IV)

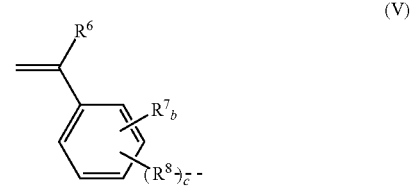

(V)

wherein each $R^4$ and $R^6$ are independently a hydrogen or a methyl group; wherein each $R^5$ and $R^8$ are independently a $C_{1-10}$ alkylene group; wherein each $R^7$ is independently a $C_{1-10}$ alkyl group; wherein b is 0 to 4 and wherein c is 0 or 1.

The present invention provides a color cosmetic formulation, comprising: a color ingredient; 30 to 92 wt % of a dermatologically acceptable carrier; and 0.1 to 10 wt %, on a solids basis, of a polymer blend of the present invention; wherein the polymer blend comprises: a single stage polymer, and a silicone-grafted vinyl copolymer; wherein the single stage polymer comprises: 90 to 99.8 wt %, based on weight of the single stage polymer, of structural units of a monoethylenically unsaturated non-ionic monomer; 0.19 to 10 wt %, based on weight of the single stage polymer, of structural units of a monoethylenically unsaturated carboxylic acid monomer; and 0.01 to 2 wt %, based on weight of the single stage polymer, of structural units of a multiethylenically unsaturated monomer having at least two ethylenically unsaturated groups per molecule; and wherein the silicone-grafted vinyl copolymer, comprises: 25 to 95 wt %, based on weight of the silicone-grafted vinyl copolymer, of structural units of a vinyl monomer; 5 to 75 wt %, based on weight of the silicone-grafted vinyl copolymer, of structural units of a carbosiloxane dendrimer of formula (I); wherein each $R^1$ is independently selected from the group consisting of a $C_{1-10}$ alkyl group and an aryl group; wherein each X is a silylalkyl group of formula (II); wherein $R^2$ is a $C_{2-10}$ alkylene group; wherein each $R^3$ is independently a $C_{1-10}$ alkyl group; wherein each Z is independently selected from the group consisting of a hydrogen, a $C_{1-10}$ alkyl group, an aryl group and a silylalkyl group of formula (II); wherein a is 0 to 3; wherein Y is selected from the group consisting of formula (III), (IV) and (V); wherein each $R^4$ and $R^6$ are independently a hydrogen or a methyl group; wherein each $R^5$ and $R^8$ are independently a $C_{1-10}$ alkylene group; wherein each $R^7$ is independently a $C_{1-10}$ alkyl group; wherein b is 0 to 4 and wherein c is 0 or 1.

DETAILED DESCRIPTION

We have surprisingly found a synergistic polymer blend of a single stage polymer and a silicone-grafted vinyl copolymer, as described in greater detail herein, provide enhanced wear resistance for color retention when used in combination with a color ingredient in color cosmetic formulations and also provide enhanced SPF protection when used in combination with a suncare active.

Unless otherwise indicated, ratios, percentages, parts, and the like are by weight.

The term "aesthetic characteristics" as used herein and in the appended claims in reference to a color cosmetic formulation refers to visual and tactile sensory properties (e.g., smoothness, tack, lubricity, texture, color, clarity, tubridity, uniformity).

The term "structural units" as used herein and in the appended claims refers to the remnant of the indicated monomer in the claimed polymer; thus a structural unit of ethyl acrylate is illustrated:

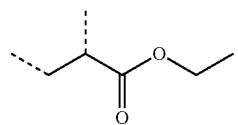

where the dotted lines represent the points of attachment to the polymer backbone.

The term "(meth)acrylic acid" as used herein and in the appended claims is intended to serve as a generic expression embracing both acrylic acid and methacrylic acid.

The term "(meth)acrylate" as used herein and in the appended claims is intended to serve as a generic expression embracing both acrylate and methacrylate.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the color cosmetic formulation of the present invention, comprises: a color ingredient; and a polymer blend, comprising (preferably, 25 to 95 wt % (more preferably, 30 to 90 wt %; still more preferably, 50 to 80 wt %; most preferably, 60 to 70 wt %), based on weight solids of the polymer blend, of) a single stage polymer, and (preferably, 5 to 75 wt % (preferably, 10 to 70 wt %; more preferably, 20 to 50 wt %; most preferably, 30 to 40 wt %), based on weight solids of the polymer blend, of) a silicone-grafted vinyl copolymer, wherein the single stage polymer comprises: 90 to 99.8 wt % (preferably, 95 to 99.5 wt %; more preferably, 97 to 99.25 wt %; most preferably, 98 to 99 wt %) of structural units of a monoethylenically unsaturated non-ionic monomer; 0.19 to 10 wt % (preferably, 0.45 to 5 wt %; more preferably, 0.65 to 3 wt %; most preferably, 0.92 to 2 wt %) of structural units of a monoethylenically unsaturated carboxylic acid monomer; and 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %) of structural units of a multiethylenically unsaturated monomer having at least two ethylenically unsaturated groups per molecule; and wherein the silicone-grafted vinyl copolymer, comprises: 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer; and 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I)

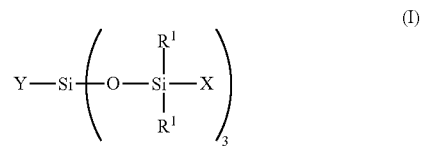

wherein each $R^1$ is independently selected from the group consisting of a $C_{1\text{-}10}$ alkyl group and an aryl group; wherein each X is a silylalkyl group of formula (II)

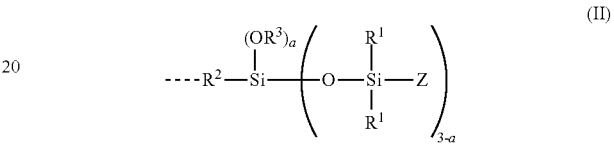

wherein $R^2$ is a $C_{2\text{-}10}$ alkylene group; wherein each $R^3$ is independently a $C_{1\text{-}10}$ alkyl group; wherein each Z is independently selected from the group consisting of a hydrogen, a $C_{1\text{-}10}$ alkyl group, an aryl group and a silylalkyl group of formula (II); wherein a is 0 to 3; wherein Y is selected from the group consisting of formula (III), (IV) and (V)

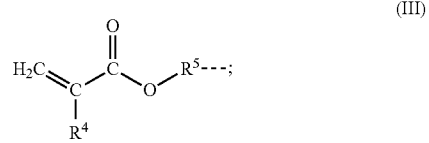

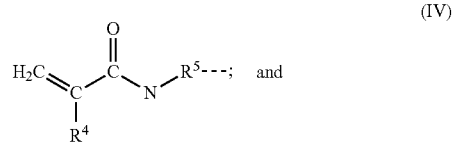

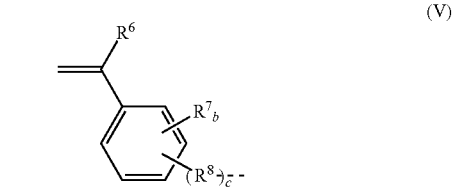

wherein each $R^4$ and $R^6$ are independently a hydrogen or a methyl group; wherein each $R^5$ and $R^8$ are independently a $C_{1\text{-}10}$ alkylene group; wherein each $R^7$ is independently a $C_{1\text{-}10}$ alkyl group; wherein b is 0 to 4 and wherein c is 0 or 1.

Preferably, the color cosmetic formulation of the present invention, comprises: 30 to 92 wt % (preferably, 35 to 92 wt %; more preferably, 40 to 80 wt %) of a dermatologically acceptable carrier; a color ingredient; and 0.1 to 10 wt % (preferably, 0.5 to 7.5 wt %; more preferably, 1 to 7 wt %; still more preferably, 3 to 5 wt %; most preferably, 3.5 to 4.5 wt %), on a solids basis, of a polymer blend; wherein the polymer blend, comprises: (preferably, 25 to 95 wt % (more preferably, 30 to 90 wt %; still more preferably, 50 to 80 wt %; most preferably, 60 to 70 wt %), based on weight solids of the polymer blend, of) a single stage polymer, and (preferably, 5 to 75 wt % (preferably, 10 to 70 wt %; more preferably, 20 to 50 wt %; most preferably, 30 to 40 wt %), based on weight solids of the polymer blend, of) a silicone-grafted vinyl copolymer, wherein the single stage polymer comprises: 90 to 99.8 wt % (preferably, 95 to 99.5 wt %; more preferably, 97 to 99.25 wt %; most preferably, 98 to 99 wt %) of structural units of a monoethylenically unsaturated non-ionic monomer; 0.19 to 10 wt % (preferably, 0.45 to 5 wt %; more preferably, 0.65 to 3 wt %; most preferably, 0.92 to 2 wt %) of structural units of a monoethylenically unsaturated carboxylic acid monomer; and 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %) of structural units of a multiethylenically unsaturated monomer having at least two ethylenically unsaturated groups per molecule; and wherein the silicone-grafted vinyl copolymer, comprises: 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer; and 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I); wherein each $R^1$ is independently selected from the group consisting of a $C_{1-10}$ alkyl group and an aryl group; wherein each X is a silylalkyl group of formula (II); wherein $R^2$ is a $C_{2-10}$ alkylene group; wherein each $R^3$ is independently a $C_{1-10}$ alkyl group; wherein each Z is independently selected from the group consisting of a hydrogen, a $C_{1-10}$ alkyl group, an aryl group and a silylalkyl group of formula (II); wherein a is 0 to 3; wherein Y is selected from the group consisting of formula (III), (IV) and (V); wherein each $R^4$ and $R^6$ are independently a hydrogen or a methyl group; wherein each $R^5$ and $R^8$ are independently a $C_{1-10}$ alkylene group; wherein each $R^7$ is independently a $C_{1-10}$ alkyl group; wherein b is 0 to 4 and wherein c is 0 or 1.

Preferably, the color cosmetic formulation of the present invention, comprises 30 to 92 wt % (preferably, 35 to 92 wt %; more preferably, 40 to 80 wt %) of a dermatologically acceptable carrier. More preferably, the color cosmetic formulation of the present invention, comprises 30 to 92 wt % (preferably, 35 to 92 wt %; more preferably, 40 to 80 wt %) of a dermatologically acceptable carrier; wherein the color ingredient and the polymer blend are dispersed in the dermatologically acceptable carrier. Still more preferably, the color cosmetic formulation of the present invention, comprises 30 to 92 wt % (preferably, 35 to 92 wt %; more preferably, 40 to 80 wt %) of a dermatologically acceptable carrier; wherein the color ingredient and the polymer blend are dispersed in the dermatologically acceptable carrier. Most preferably, the color cosmetic formulation of the present invention, comprises 30 to 92 wt % (preferably, 35 to 92 wt %; more preferably, 40 to 80 wt %) of a dermatologically acceptable carrier; wherein the color ingredient and the polymer blend are dispersed in the dermatologically acceptable carrier.

Preferably, the color cosmetic formulation of the present invention, comprises 30 to 92 wt % (preferably, 35 to 92 wt %; more preferably, 40 to 80 wt %) of a dermatologically acceptable carrier; wherein the dermatologically acceptable carrier is selected to be capable of evaporating upon application of the color cosmetic formulation to mammalian skin (preferably, human skin).

Preferably, the color cosmetic formulation of the present invention, comprises 30 to 92 wt % (preferably, 35 to 92 wt %; more preferably, 40 to 80 wt %) of a dermatologically acceptable carrier; wherein the dermatologically acceptable is selected from the group consisting of water (e.g., deionized, distilled water); emulsions (e.g., oil-in-water emulsion, water-in-oil emulsion); alcohols (e.g., CIA straight or branched chain alcohols such as methyl alcohol, ethyl alcohol, propyl alcohol, isopropyl alcohol, butyl alcohol); glycols (e.g., ethylene glycol, propylene glycol, butylene glycol, pentylene glycol, hexylene glycol, dipropylene glycol, ethoxy diglycol); glycerin; acetone; methyl acetate; butyl cellosolve and mixtures thereof. More preferably, the color cosmetic formulation of the present invention, comprises 30 to 92 wt % (preferably, 35 to 92 wt %; more preferably, 40 to 80 wt %) of a dermatologically acceptable carrier; wherein the dermatologically acceptable carrier includes water (preferably, at least one of deionized water and distilled water; more preferably, deionized, distilled water).

Preferably, the color cosmetic formulation of the present invention comprises a color ingredient. More preferably, the color cosmetic formulation of the present invention comprises a color ingredient; wherein the color ingredient is selected from the group consisting of inorganic pigments, organic pigments, aqueous pigment dispersions and mixtures thereof. Still more preferably, the color cosmetic formulation of the present invention comprises a color ingredient; wherein the color ingredient is selected from the group consisting of Ext. D&C Yellow No. 2, Ext. D & C Violet No. 2, FD&C Red No. 4, FD&C Red No. 40, FD&C Yellow No. 5, FD&C Yellow No. 6, FD&C Green No. 3, FD&C Blue No. 1, D&C Yellow No. 7, D&C Yellow No. 8, D&C Yellow No. 10, D&C Yellow No. 11, D&C Violet No. 2, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 34, D&C Red No. 33, D&C Red No. 36, D&C Green No. 5, D&C Green No. 6, D&C Green No. 8, D&C Blue No. 4, D&C Orange No. 4, D&C Orange No. 5, D&C Orange No. 10, D&C Orange No. 11, D&C Brown No. 1, Aluminum powder, Annatto, Bismuth citrate, Bismuth Oxychloride, Bronze powder, Caramel, Carmine, β-Carotene, Chromium hydroxide green, Chromium oxide green, Copper chlorophyllin, Copper powder, Dihydroxyacetone, Ferric Ammonium ferrocyanide, Ferric ferrocyanide, Guanine, Iron oxide, Manganese Violet, Mica, Silver, Titanium Dioxide, Ultramarine, Zinc Oxide and mixtures thereof. Still more preferably, the color cosmetic formulation of the present invention comprises a color ingredient; wherein the color ingredient includes at least one iron oxide. Most preferably, preferably, the color cosmetic formulation of the present invention comprises a color ingredient; wherein the color ingredient includes a mixture of iron oxides.

Preferably, the color cosmetic formulation of the present invention comprises a polymer blend. More preferably, the color cosmetic formulation of the present invention comprises 0.1 to 10 wt % (preferably, 0.5 to 7.5 wt %; more preferably, 1 to 7 wt %; still more preferably, 3 to 5 wt %; most preferably, 3.5 to 4.5 wt %) a polymer blend of a single stage polymer and a silicone-grafted vinyl copolymer.

Preferably, the polymer blend of the present invention comprises a single stage polymer. More preferably, the polymer blend of the present invention, comprises 25 to 95 wt % (preferably, 30 to 90 wt %; more preferably, 50 to 80 wt %; most preferably, 60 to 70 wt %), based on weight solids of the polymer blend, a single stage polymer. Most preferably, the polymer blend of the present invention, comprises: 25 to 95 wt % (preferably, 30 to 90 wt %; more preferably, 50 to 80 wt %; most preferably, 60 to 70 wt %), based on weight solids of the polymer blend, of a single stage polymer; wherein the single stage polymer comprises: 90 to 99.8 wt % (preferably, 95 to 99.5 wt %; more preferably, 97 to 99.25 wt %; most preferably, 98 to 99 wt %) of structural units of a monoethylenically unsaturated non-ionic monomer; 0.19 to 10 wt % (preferably, 0.45 to 5 wt %; more preferably, 0.65 to 3 wt %; most preferably, 0.92 to 2 wt %) of structural units of a monoethylenically unsaturated carboxylic acid monomer; and 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %) of structural units of a multiethylenically unsaturated monomer having at least two ethylenically unsaturated groups per molecule.

Preferably, the single stage polymer of the present invention comprises 90 to 99.8 wt % (preferably, 95 to 99.5 wt %; more preferably, 97 to 99.25 wt %; most preferably, 98 to 99 wt %) of structural units of a monoethylenically unsaturated non-ionic monomer; wherein the monoethylenically unsaturated non-ionic monomer is selected from the group consisting of a mixture of (i) a $C_{1-5}$ alkyl (meth)acrylate and (ii) a $C_{6-22}$ alkyl (meth)acrylate. More preferably, the single stage polymer of the present invention comprises 90 to 99.8 wt % (preferably, 95 to 99.5 wt %; more preferably, 97 to 99.25 wt %; most preferably, 98 to 99 wt %) of structural units of a monoethylenically unsaturated non-ionic monomer; wherein the monoethylenically unsaturated non-ionic monomer is selected from the group consisting of a mixture of (i) 35 to 75 wt % (preferably, 40 to 70 wt %; more preferably, 50 to 65 wt %; still more preferably, 55 to 62 wt %; yet more preferably, 58 to 61 wt %; most preferably, 59 to 60 wt %) of a $C_{1-5}$ alkyl (meth)acrylate and (ii) 25 to 65 (preferably, 30 to 60 wt %; more preferably, 35 to 50 wt %; still more preferably, 38 to 45 wt %; yet more preferably, 39 to 42 wt %; most preferably, 40 to 41 wt %) of a $C_{8-22}$ alkyl (meth)acrylate. Still more preferably, the single stage polymer of the present invention comprises 90 to 99.8 wt % (preferably, 95 to 99.5 wt %; more preferably, 97 to 99.25 wt %; most preferably, 98 to 99 wt %) of structural units of a monoethylenically unsaturated non-ionic monomer; wherein the monoethylenically unsaturated non-ionic monomer is selected from the group consisting of a mixture of (i) 35 to 75 wt % (preferably, 40 to 70 wt %; more preferably, 50 to 65 wt %; still more preferably, 55 to 62 wt %; yet more preferably, 58 to 61 wt %; most preferably, 59 to 60 wt %) of a $C_{1-4}$ alkyl (meth)acrylate; wherein the $C_{1-4}$ alkyl (meth)acrylate is selected from the group consisting of methyl (meth)acrylate, ethyl (meth)acrylate, n-butyl (meth)acrylate, i-butyl (meth)acrylate, t-butyl (meth)acrylate, mixtures thereof; and (ii) 25 to 65 (preferably, 30 to 60 wt %; more preferably, 35 to 50 wt %; still more preferably, 38 to 45 wt %; yet more preferably, 39 to 42 wt %; most preferably, 40 to 41 wt %) of a $C_{8-22}$ alkyl (meth)acrylate; wherein the $C_{8-22}$ alkyl (meth)acrylate is selected from the group consisting of cyclo-hexyl (meth)acrylate, 2-ethylhexyl (meth)acrylate, lauryl (meth)acrylate, oleyl (meth)acrylate, palmityl (meth)acrylate, stearyl (meth)acrylate, isodecyl (meth)acrylate, behenyl (meth)acrylate, cetyl-eicosyl (meth)acrylate and mixtures thereof. Most preferably, wherein the monoethylenically unsaturated non-ionic monomer is selected from the group consisting of a mixture of (i) 35 to 75 wt % (preferably, 40 to 70 wt %; more preferably, 50 to 65 wt %; still more preferably, 55 to 62 wt %; yet more preferably, 58 to 61 wt %; most preferably, 59 to 60 wt %) of a $C_{1-4}$ alkyl (meth)acrylate, wherein the $C_{1-4}$ alkyl (meth)acrylate a mixture of 30 to 40 wt % (preferably, 32 to 36 wt %; more preferably, 33 to 35 wt %; most preferably, 33.9 to 34.5 wt %) of methyl (meth)acrylate and 60 to 70 wt % (preferably, 64 to 68 wt %; more preferably, 65 to 67 wt %; most preferably, 65.5 to 66.1 wt %) of n-butyl (meth)acrylate; and (ii) 25 to 65 (preferably, 30 to 60 wt %; more preferably, 35 to 50 wt %; still more preferably, 38 to 45 wt %; yet more preferably, 39 to 42 wt %; most preferably, 40 to 41 wt %) of a $C_{8-22}$ alkyl (meth)acrylate, wherein the $C_{8-22}$ alkyl (meth)acrylate is selected from the group consisting of ethylhexyl (meth)acrylate, lauryl (meth)acrylate, stearyl (meth)acrylate and mixtures thereof (preferably, wherein the $C_{8-22}$ alkyl (meth)acrylate is selected from the group consisting of 2-ethylhexyl acrylate, lauryl methacrylate, stearyl methacrylate and mixtures thereof; more preferably, wherein the $C_{8-22}$ alkyl (meth)acrylate includes 2-ethylhexyl acrylate; most preferably, wherein the $C_{8-22}$ alkyl (meth)acrylate is 2-ethylhexyl acrylate).

Preferably, the single stage polymer of the present invention comprises 0.19 to 10 wt % (preferably, 0.45 to 5 wt %; more preferably, 0.65 to 3 wt %; most preferably, 0.92 to 2 wt %) of structural units of a monoethylenically unsaturated carboxylic acid monomer; wherein the monoethylenically unsaturated carboxylic acid monomer is selected from the group consisting of (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate, and other derivatives such as corresponding anhydride, amides and esters. More preferably, the single stage polymer of the present invention comprises 0.19 to 10 wt % (preferably, 0.45 to 5 wt %; more preferably, 0.65 to 3 wt %; most preferably, 0.92 to 2 wt %) of structural units of a monoethylenically unsaturated carboxylic acid monomer; wherein the monoethylenically unsaturated carboxylic acid monomer is selected from the group consisting of acrylic acid, methacrylic acid, itaconic acid, crotonic acid and mixtures thereof. Still more preferably, the single stage polymer of the present invention comprises 0.19 to 10 wt % (preferably, 0.45 to 5 wt %; more preferably, 0.65 to 3 wt %; most preferably, 0.92 to 2 wt %) of structural units of a monoethylenically unsaturated carboxylic acid monomer; wherein the monoethylenically unsaturated carboxylic acid monomer is selected from the group consisting of at least one of acrylic acid and methacrylic acid. Most preferably, the single stage polymer of the present invention comprises 0.19 to 10 wt % (preferably, 0.45 to 5 wt %; more preferably, 0.65 to 3 wt %; most preferably, 0.92 to 2 wt %) of structural units of a monoethylenically unsaturated carboxylic acid monomer; wherein the monoethylenically unsaturated carboxylic acid monomer is selected from the group consisting of at least one of acrylic acid and methacrylic acid; wherein 75 to 100 mol % (preferably, 85 to 100 mol %; more preferably, 95 to 100 mol %; still more preferably, >99 mol %; most preferably, 100 mol %) of the monoethylenically unsaturated carboxylic acid monomer is methacrylic acid.

Preferably, the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %) of structural units of a multiethylenically unsaturated monomer having at least two ethylenically unsaturated groups per molecule; wherein the multiethylenically unsaturated monomer having at least two ethylenically unsaturated groups per molecule is selected from the group consisting of divinylaromatic compounds, di-(meth)acrylate esters, tri-(meth)acrylate esters, tetra-(methacrylate)esters, di-allyl ethers, tri-allyl ethers, tetra-allyl ethers, di-allyl esters, tri-allyl esters, tetra-allyl esters, allyl (meth)acrylate and mixtures thereof. More preferably, the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %) of structural units of a multiethylenically unsaturated monomer having at least two ethylenically unsaturated groups per molecule; wherein the multiethylenically unsaturated monomer having at least two ethylenically unsaturated groups per molecule is selected from the group consisting of divinylbenzene (DVB), trimethylolpropane diallyl ether, tetra-allyl pentaerythritol, triallyl pentaerythritol, diallyl pentaerythritol, dially phthalate, diallyl maleate, triallyl cyanurate, Bisphenol A diallyl ether, allyl sucroses, methylene bisacrylamide, trimethylolpropane triacrylate, allyl methacrylate (ALMA), ethylene glycol dimethacrylate (EGDMA), hexane-1,6-diol diacrylate (HDDA), butylene glycol dimethacrylate (BGDMA) and mixtures thereof. Still more preferably, the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %) of structural units of a multiethylenically unsaturated monomer having at least two ethylenically unsaturated groups per molecule; wherein the multiethylenically unsaturated monomer having at least two ethylenically unsaturated groups per molecule is selected from the group consisting of DVB, ALMA, EGDMA, HDDA and BGDMA. Yet more preferably, the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %) of structural units of a multiethylenically unsaturated monomer having at least two ethylenically unsaturated groups per molecule; wherein the multiethylenically unsaturated monomer having at least two ethylenically unsaturated groups per molecule includes ALMA. Most preferably, the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %) of structural units of a multiethylenically unsaturated monomer having at least two ethylenically unsaturated groups per molecule; wherein the multiethylenically unsaturated monomer having at least two ethylenically unsaturated groups per molecule is ALMA.

Preferably, the polymer blend of the present invention comprises a silicone-grafted vinyl copolymer. More preferably, the polymer blend of the present invention, comprises 5 to 75 wt % (preferably, 10 to 70 wt %; more preferably, 20 to 50 wt %; most preferably, 30 to 40 wt %), based on weight solids of the polymer blend, of a silicone-grafted vinyl copolymer; wherein the silicone-grafted vinyl copolymer comprises: 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer; and 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I). Most preferably, the polymer blend of the present invention, comprises 5 to 75 wt % (preferably, 10 to 70 wt %; more preferably, 20 to 50 wt %; most preferably, 30 to 40 wt %), based on weight solids of the polymer blend, of a silicone-grafted vinyl copolymer; wherein the silicone-grafted vinyl copolymer comprises: 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer; and 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I); wherein the silicone-grafted vinyl copolymer is an acrylates/polytrimethylsiloxymethacrylate copolymer.

Preferably, the silicone-grafted vinyl copolymer of the present invention comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer. More preferably, the silicone-grafted vinyl copolymer of the present invention comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer; wherein the vinyl monomer contains at least one radically polymerizable vinyl group per molecule. Still more preferably, the silicone-grafted vinyl copolymer of the present invention comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer; wherein the vinyl monomer is selected from the group consisting of $C_{1-3}$ alkyl acrylates (e.g., methyl acrylate, ethyl acrylate, n-propyl acrylate, isopropyl acrylate); $C_{1-3}$ alkyl methacrylates (e.g., methyl methacrylate, ethyl methacrylate, n-propyl methacrylate, isopropyl methacrylate); $C_{4-20}$ alkyl acrylates (e.g., n-butyl acrylate, isobutyl acrylate, tert-butyl acrylate, n-hexyl acrylate, cyclohexyl acrylate, 2-ethylhexyl acrylate, octyl acrylate, lauryl acrylate, stearyl acrylate); $C_{4-20}$ alkyl methacrylates (e.g., n-butyl methacrylate, isobutyl methacrylate, tert-butyl methacrylate, n-hexyl methacrylate, cyclohexyl methacrylate, 2-ethylhexyl methacrylate, octyl methacrylate, lauryl methacrylate, stearyl methacrylate); vinyl esters of lower aliphatic acids (e.g., vinyl acetate, vinyl propionate); vinyl esters of higher aliphatic acids (e.g., vinyl butyrate, vinyl caproate, vinyl-2-ethylhexanoate, vinyl laurate, vinyl stearate); aromatic vinyl monomers (e.g., styrene, vinyl toluene, benzyl acrylate, benzyl methacrylate, phenoxyethyl acrylate, phenoxyethyl methacrylate, vinyl pyrrolidone); amino functional vinyl monomers (e.g., dimethylaminoethyl acrylate, dimethylaminoethyl methacrylate, diethylaminoethyl acrylate, and diethylaminoethyl methacrylate); amide functional vinyl monomers (e.g., acrylamide, N-methylolacrylamide, N-methoxymethylacrylamide, isobutoxymethoxyacrylamide, N,N-dimethylacrylamide, methacrylamide, N-methylolmethacrylamide, N-methoxymethylmethacrylamide, obutoxymethoxymethacrylamide, N,N-dimethylmethacrylamide); hydroxyl-functional vinyl monomers (e.g., 2-hydroxy ethyl acrylate, 2-hydroxybutyl acrylate, 2-hydroxypropyl acrylate, 2-hydroxyethyl methacrylate, 2-hydroxybutyl methacrylate, 2-hydroxypropyl methacrylate); fluorinated vinyl monomers (e.g., trifluoropropyl acrylate, perfluorobutylethyl acrylate, perfluorooctylethyl acrylate, trifluoropropyl methacrylate, perfluorobutylethyl methacrylate, perfluorooctylethyl methacrylate); epoxy-functional vinyl monomers (e.g., glycidyl acrylate, 3,4-epoxycyclohexylmethyl acrylate, glycidyl methacrylate, 3,4-epoxycyclohexylmethyl methacrylate); ether linkage containing vinyl monomers (e.g., tetrahydrofurfuryl acrylate, butoxy ethyl acrylate, ethoxy diethylene glycol acrylate, polyethylene glycol acrylate, polypropylene glycol monoacrylate, hydroxybutyl vinyl ether, cetyl vinyl ether, 2-ethylhexyl vinyl ether, tetrahydrofurfuryl methacrylate, butoxyethyl methacrylate, ethoxydiethyleneglycol methacrylate, polyethylene glycol methacrylate, polypropyleneglycol monomethacrylate); alkoxysilanes that contain a radically polymerizable unsaturated group (e.g., $CH_2=CHCOOC_3H_6Si(OCH_3)_3$, $CH_2=C(CH_3)COOC_3H_6Si(OCH_3)_3$, $CH_2=C(CH_3)COOC_3H_6Si(CH_3)(OCH_3)_2$, $CH_2=C(CH_3)COOC_3H_6Si(CH_3)_2OCH_3$, $CH_2=C(CH_3)COOC_2H_4OC_3H_6Si(OCH_3)_3$, $CH_2=C(CH_3)COOC_{12}H_{24}Si(OCH_3)_3$, $CH_2=CHOC_3H_6Si(CH_3)(OC_2H_5)_2$, $CH_2=CHSi(OCH_3)_3$, $CH_2=CHSi(OC_2H_5)_3$, $CH_2=CHSi(C_4H_9)(OC_4H_9)_2$); unsaturated group-functionalized silicone compounds (e.g., branched or straight chain organopolysiloxane bearing an acryl or methacryl group at a single terminal; polydimethylsiloxane bearing a styryl group at a single terminal); butadiene; vinyl chloride; vinylidene chloride; acrylonitrile; methacrylonitrile; dibutyl fumarate; maleic anhydride, dodecylsuccinic anhydride; radically polymerizable unsaturated carboxylic acids (e.g., acrylic acid, methacrylic acid, itaconic acid, crotonic acid, fumaric acid, maleic acid, as well as their alkali metal salts, ammonium salts and organic amine salts); radically polymerizable unsaturated monomers containing a sulfonic acid residue (e.g., styrene sulfonic acid, as well as their alkali metal salts, ammonium salts and organic amine salts); quaternary ammonium salts that are derived from (meth) acrylic acid (e.g., 2-hydroxy-3-methacryloxypropyltrimethylammonium chloride); methacrylate esters of alcohols that contain a tertiary amine group (e.g., diethylamine ester of methacrylic acid, as well as the quaternary ammonium salts thereof); and mixtures thereof. Yet more preferably, the silicone-grafted vinyl copolymer of the present invention comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer; wherein the vinyl monomer is selected from the group consisting of $C_{1-3}$ alkyl acrylates (e.g., methyl acrylate, ethyl acrylate, n-propyl acrylate, isopropyl acrylate); $C_{1-3}$ alkyl methacrylates (e.g., methyl methacrylate, ethyl methacrylate, n-propyl methacrylate, isopropyl methacrylate); $C_{4-20}$ alkyl acrylates (e.g., n-butyl acrylate, isobutyl acrylate, tert-butyl acrylate, n-hexyl acrylate, cyclohexyl acrylate, 2-ethylhexyl acrylate, octyl acrylate, lauryl acrylate, stearyl acrylate); $C_{4-20}$ alkyl methacrylates (e.g., n-butyl methacrylate, isobutyl methacrylate, tert-butyl methacrylate, n-hexyl methacrylate, cyclohexyl methacrylate, 2-ethylhexyl methacrylate, octyl methacrylate, lauryl methacrylate, stearyl methacrylate); aromatic vinyl monomers (e.g., styrene, vinyl toluene, benzyl acrylate, benzyl methacrylate, phenoxyethyl acrylate, phenoxyethyl methacrylate, vinyl pyrrolidone); and mixtures thereof. Yet still more preferably, the silicone-grafted vinyl copolymer of the present invention comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl monomer; wherein the vinyl monomer is selected from the group consisting of methyl acrylate, ethyl acrylate, n-propyl acrylate, isopropyl acrylate, methyl methacrylate, ethyl methacrylate, n-propyl methacrylate, isopropyl methacrylate, n-butyl acrylate, isobutyl acrylate, tert-butyl acrylate, n-hexyl acrylate, cyclohexyl acrylate, 2-ethylhexyl acrylate, n-butyl methacrylate, isobutyl methacrylate, tert-butyl methacrylate, n-hexyl methacrylate, 2-ethylhexyl methacrylate, styrene and mixtures thereof. Most preferably, the silicone-grafted vinyl copolymer of the present invention comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of vinyl monomer; wherein the vinyl monomer includes methyl methacrylate and butyl acrylate.

Preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I). More preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I); wherein each $R^1$ is independently selected from the group consisting of a $C_{1-10}$ alkyl group and an aryl group (preferably, wherein each $R^1$ is a methyl group); wherein each X is a silylalkyl group of formula (II); wherein $R^2$ is a $C_{2-10}$ alkylene group (preferably, wherein $R^2$ is a $C_{2-5}$ alkylene group; more preferably, wherein $R^2$ is a $C_{2-4}$ alkylene group; most preferably, wherein $R^2$ is a $C_2$ alkylene group); wherein each $R^3$ is independently a $C_{1-10}$ alkyl group (preferably, wherein each $R^3$ is independently a $C_{1-5}$ alkyl group; more preferably, wherein each $R^3$ is independently a $C_{1-4}$ alkyl group; most preferably, wherein each $R^3$ is a methyl group); wherein each Z is independently selected from the group consisting of a hydrogen, a $C_{1-10}$ alkyl group, an aryl group and a silylalkyl group of formula (II) (preferably, wherein each Z is a methyl group); wherein a is 0 to 3 (preferably, wherein a is 0); wherein Y is selected from the group consisting of formula (III), (IV) and (V) (preferably, wherein Y is of formula (III)); wherein each $R^4$ and $R^6$ are independently a hydrogen or a methyl group (preferably; wherein each $R^4$ and $R^6$ are a methyl group); wherein each $R^5$ and $R^8$ are independently a $C_{1-10}$ alkylene group (preferably, wherein each $R^5$ and $R^8$ are independently a $C_{2-5}$ alkylene group; more preferably, wherein each $R^5$ and $R^8$ are independently a $C_{2-4}$ alkylene group; most preferably, wherein each $R^5$ and $R^8$ are independently a $C_3$ alkylene group); wherein each $R^7$ is independently a $C_{1-10}$ alkyl group (preferably, wherein each $R^7$ is independently a $C_{1-5}$ alkyl group; more preferably, wherein each $R^7$ is independently a $C_{1-4}$ alkyl group; most preferably, wherein each $R^7$ is a methyl group); wherein b is 0 to 4; wherein c is 0 or 1. Still more preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I); wherein Y is selected from the group consisting of acryloxymethyl, 3-acryloxypropyl, methacryloxymethyl, 3-methyacryloxypropyl, 4-vinylphenyl, 3-vinylphenyl, 4-(2-propenyl)phenyl, 3-(2-propenyl)phenyl, 2-(4-vinylphenyl)ethyl and 2-(3-vinylphenyl)ethyl. Yet more preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I); wherein Y is selected from the group consisting of acryloxymethyl, 3-acryloxypropyl, methacryloxymethyl and 3-methyacryloxypropyl. Still yet more preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I); wherein Y is selected from the group consisting of 3-acryloxypropyl and 3-methyacryloxypropyl. Most preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (I); wherein each $R^1$ is a methyl group; wherein $R^2$ is a $C_2$ alkylene group; wherein a is 0; wherein each Z is a methyl group; wherein Y is of formula (III); wherein $R^4$ is a methyl group and wherein $R^5$ is a $C_3$ alkylene group.

Preferably, the color cosmetic formulation of the present invention, further comprises a suncare active. More preferably, the color cosmetic formulation of the present invention further comprises a suncare active; wherein the suncare active is a UV radiation absorbing agent. Still more preferably, the color cosmetic formulation of the present invention, further comprises a suncare active, wherein the suncare active is a UV radiation absorbing agent selected from the group consisting of physical blockers (e.g., red petrolatum, titanium dioxide, zinc oxide) and chemical absorbers (e.g., 1-(4-methoxyphenol)-3-(4-tert-butylphenyl)propane-1,3-dione (INCI: Butyl Methoxydibenzoylmethane); 2-hydroxy-4-methoxybenzophenone (INCI: Benzophenone-3); dioxybenzone; sulisobenzone; menthyl anthranilate; para-aminobenzoic acid; amyl paradimethylaminobenzoic acid; octyl para-dimethylaminobenzoate; ethyl 4-bis (hydroxypropyl) para-aminobenzoate; polyethylene glycol (PEG-25) para-aminobenzoate; ethyl 4-bis (hydroxypropyl) aminobenzoate; diethanolamine para-methyoxycinnamate; 2-ethoxyethyl para-methoxycinnamate; ethylhexyl para-methoxycinnamate; octyl para-methoxycinnamate; isoamyl para-methoxycinnamate; 2-ethylhexyl-2-cyano-3,3-diphenyl-acrylate; 2-ethylhexyl-2-cyano-3,3-diphenyl-2-propenoate (INCI: octocrylene); 2-ethylhexyl-2-hydroxybenzoate (INCI: Ethylhexyl Salicylate); homomenthyl salicylate; glyceryl aminobenzoate; triethanolamine salicylate; digalloyl trioleate; lawsone with dihydroxy acetone; 2-phenylbenzimidazole-5-sulfonic acid; 4-methylbenzylidine camphor; avobenzone; triazines; benzotriazoles; vinyl group-containing amides; cinnamic acid amides; sulfonated benzimidazoles); 3,3,5-trimethylcyclohexyl 2-hydroxybenzoate (INCI: Homosalate). Yet more preferably, the color cosmetic formulation of the present invention, further comprises of a suncare active, wherein the suncare active is a UV radiation absorbing agent comprises a mixture of UV radiation absorbing agents. Most preferably, the color cosmetic formulation of the present invention, comprises a suncare active, wherein the suncare active is a UV radiation absorbing agent is a mixture of UV absorbing agents including at least one of titanium dioxide; 1-(4-methoxyphenol)-3-(4-tert-butylphenyl)propane-1,3-dione; 2-ethylhexyl-2-hydroxybenzoate; 2-ethylhexyl-2-cyano-3,3-diphenyl-2-propenoate; 2-hydroxy-4-methoxybenzophenone and 3,3,5-trimethylcyclohexyl 2-hydroxybenzoate.

Preferably, the color cosmetic formulation of the present invention, optionally, further comprises an optional additive. More preferably, the color cosmetic formulation of the present invention, further comprises an optional additive, wherein the optional additive is selected from the group consisting of water proofing agents, emollients, preservatives, antioxidants, fragrances, humectants, rheology modifiers, aesthetic modifiers, vitamins, skin protectants, oils, emulsifiers, surfactants, pearlizers, consistency factors, thickeners, super fatting agents, stabilizers, polymers, silicone compounds, fats, waxes, lecithins, phospholipids, fillers, light management powders and particles, and mixtures thereof.

Preferably, the color cosmetic formulation of the present invention has a pH of 4 to 9. More preferably, the color cosmetic formulation of the present invention has a pH of 4.5 to 8.5. Still more preferably, the color cosmetic formulation of the present invention has a pH of 5.0 to 8.0. Most preferably, the color cosmetic formulation of the present invention has a pH of 5.5 to 7.5.

Preferably, the color cosmetic formulation of the present invention is provided a product form selected from the group consisting of a cream, an aqueous solution, an oil, an ointment, a paste, a gel, a lotion, a milk, a foam, a stick and a suspension.

The color cosmetic formulation of the present invention are useful for enhancing the appearance of skin through application to the skin. Preferably, the color cosmetic formulation of the present invention applies easily to the skin, leaving a clear vivid color that remains in place at least through the work day and preferably thereafter.

Some embodiments of the present invention will now be described in detail in the following Examples.

Example S1: Single Stage Polymer

A 1-liter round-bottom flask equipped with an overhead stirrer, thermocouple, condenser and inlets for the addition of monomer and initiators was charged with deionized water (150.0 g), sodium dodecyl sulfonate surfactant (3.3 g of a 23% DS-4) and sodium carbonate (1.1 g). The flask contents were then stirred and heated at 85° C. A monomer emulsion was prepared by charging deionized water (81.1 g) and sodium dodecyl sulfonate surfactant (3.1 g of 23% DS-4) to a container and set to stir. After the surfactant was incorporated into the water, butyl acrylate (BA) (50 g), ethylhexyl acrylate (EHA) (100 g), methyl methacrylate (MMA) (96.3 g), methacrylic acid (MAA) (3.8 g) and allyl methacrylate (ALMA) (0.2 g) were added slowly to the stirring mixture in the container. A cofeed catalyst solution was also prepared by charging sodium persulfate (0.25 g) and deionized water (22 g) in another container. When the flask contents reached a temperature of 85° C., 10 g of the above prepared monomer emulsion was charged to the flask, followed with a deionized water rinse (10 g) water rinse, followed by an initiator solution of sodium persulfate (0.9 g) in deionized waiter (5.7 g). After initial polymerization and at 85° C., a monomer emulsion cofeed to the flask of the above prepared monomer emulsion was begun at a rate of 1.97 g/min. for 1.5 minutes and then at a rate of 3.93 g/min. for the next 75 minutes. Simultaneously, with the monomer emulsion cofeed the catalyst cofeed was begun at a rate of 0.24 g/min. for 92 minutes. At the completion of the cofeeds, the flask contents were chased to reduce the amount of residual monomers to provide the product single stage polymer.

Example S2: Silicone-Grafted Vinyl Copolymer

A flask equipped with an overhead stirrer, thermocouple, condenser and inlets for the addition of monomer and initiators was charged with carbosiloxane dendrimer (150 parts) with the following structure

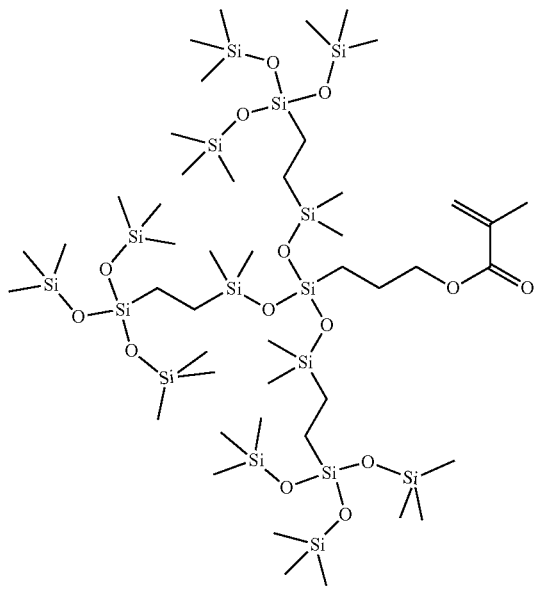

methyl methacrylate (MMA) (99 parts), n-butyl methacrylate (BMA) (51 parts) and 2-phenoxyethanol (9 parts). To the flask contents was then was added laureth-1 phosphate (7 parts), sodium hydroxide solution (4 parts, 20%) and deionized water (676 parts). The flask contents were then emulsified and dispersed using a homogenizer. The flask contents were then heated to 80° C., under a nitrogen. Upon reaching temperature, potassium persulfate (2.2 parts) was added to the flask contents while maintaining the temperature controller at 80° C. After three hours after the potassium persulfate addition, 2,2'-azobis[N-(2-carboxyethyl)-2-methylpropionamidine] tetrahydrate (2.2 parts) was added to the flask contents while maintaining the temperature controller at 80° C. The flask contents were allowed to stir for three additional hours while maintaining the temperature controller at 80° C., to provide the product silicone-grafted vinyl copolymer.

Formulation Examples G1 and G2: Generic Formulations

Skin care formulations were prepared having the generic formulations according to Formulation Examples G1 and G2 noted in TABLE 1. The carbomer and some deionized water were added to a flask and mixed until the carbomer was hydrated before adding the remainder of the Phase I ingredients. The flask contents were then heated at 75° C. with mixing. The Phase II ingredients were combined in a separate container while being heated at 75° C. with mixing until dissolved. The Phase II ingredients were then added to the flask contents with mixing until uniform. The Phase III ingredients were then added to the flask contents with mixing until uniform. The flask contents were then removed from the heating source and cooled. When the flask contents cooled below 60° C., the Phase IV ingredients were added to the flask contents with mixing until uniform. When the flask contents cooled to below 40° C., the Phase V ingredients were added to the flask contents with continued mixing until the flask contents reached ambient room temperature. The flask contents were then pH adjusted to a pH of 5.5 to 7.5, as necessary.

TABLE 1

| | | Generic Formulations | |
|---|---|---|---|
| Phase | Ingredient INCI name | Form. Ex. G1 Parts by weight (pbW) | Form. Ex. G2 Parts by weight (pbW) |
| | Deionized water | remainder to 100 | remainder to 100 |
| I | Carbomer[1] | 0.20 | 0.20 |
| I | Disodium EDTA[2] | 0.10 | 0.10 |
| I | Propylene Glycol | 2.00 | 2.00 |
| II | Avobenzone | 3.00 | 3.00 |
| II | Oxybenzone | 6.00 | 6.00 |
| II | Octyl Salicylate | 5.00 | 5.00 |
| II | Octocrylene | 10.00 | 10.00 |
| II | Hydrogenated Polydecene[3] | 7.00 | 7.00 |
| II | $C_{12-15}$ Alkyl Benzoate[4] | 5.00 | 5.00 |
| II | PEG 40 Stearate[5] | 1.00 | 1.00 |
| II | Glyceryl Stearate[6] | 1.00 | 1.00 |
| II | Cetearyl Alcohol, Ceteareth-20[7] | 1.00 | 1.00 |
| III | Triethanolamine, 99% | 0.35 | 0.35 |
| IV | Polymer to be tested (on polymer solids basis) | 1.00 | 3.00 |
| V | Preservative | 1.00 | 1.00 |

[1]Available from Rita under the tradename Acritamer 980.
[2]Available from The Dow Chemical Company under the tradename Versene NA.
[3]Available from Rita under the tradename Ritadecene 20.
[4]Available from Rita under the tradename Ritamollient TN.
[5]Available from Rita under the tradename Ritox 52.
[6]Available from Rita under the tradename Rita GMS.
[7]Available from Protameen under the tradename Procol CS-20-D.

Comparative Examples C1-C4 and Examples 1-6: Skin Care Formulations

The skin care formulations of (a) Comparative Examples C1-C2 and Examples 1-3 and (b) Comparative Examples C3-C4 and Examples 4-6 were prepared according to Formulation Examples G1 and G2 with varying test polymer as noted in TABLE 2.

TABLE 2

| Formulation | | Polymer/Polymer Blend in wt % | |
|---|---|---|---|
| Example | Formulation Example | Example S1 | Example S2 |
| Comp. Example C1 | Example G1 | 100 | 0 |
| Comp. Example C2 | Example G1 | 0 | 100 |
| Comp. Example C3 | Example G2 | 100 | 0 |
| Comp. Example C4 | Example G2 | 0 | 100 |
| Example 1 | Example G1 | 50 | 50 |
| Example 2 | Example G1 | 66.5 | 33.5 |
| Example 3 | Example G1 | 33.5 | 66.5 |
| Example 4 | Example G2 | 50 | 50 |
| Example 5 | Example G2 | 66.5 | 33.5 |
| Example 6 | Example G2 | 33.5 | 66.5 |

In-Vitro SPF Measurements

The suncare formulations prepared according to Comparative Examples C1-C4 and Examples 1-6 were each allowed to settle for one week before in-vitro SPF measurements. The in-vitro SPF performance of each of the suncare formulations was then tested in triplicate using an in-vitro technique according to the following protocol.

The substrate used for the in-vitro SPF measurements was a rough PMMA substrate (6 μm-HD6 available from Schonberg GMBH & Co. KG). The suncare formulations to be tested were each applied to three separate rough PMMA substrates using an RDS #7 wire draw down bar to provide a uniform layer of the suncare formulation over the surface of the PMMA substrate at a rate of 1.2 to 1.3 mg/cm$^2$. Each deposited layer of suncare formulation was allowed to dry for fifteen (20) minutes under ambient conditions in the laboratory. The UV absorption of each dried layer of suncare formulation between 290 nm and 400 nm was then measured at six (6) separate points using a Labsphere UV-2000S Spectrometer. The in-vitro SPF value for each suncare formulation prepared according to Comparative Examples C1-C4 and Examples 1-6 was then calculated based on the results of the UV absorption measurements. The average from the triplicate samples of each suncare formulation prepared according to Comparative Examples C1-C4 and Examples 1-6 is reported in in TABLE 3.

TABLE 3

| Example | in-vitro SPF |
| --- | --- |
| Comp. Example C1 | 150 |
| Comp. Example C2 | 236 |
| Comp. Example C3 | 230 |
| Comp. Example C4 | 257 |
| Example 1 | 347 |
| Example 2 | 321 |
| Example 3 | 246 |
| Example 4 | 332 |
| Example 5 | 421 |
| Example 6 | 342 |

Water Resistance (In-Vitro SPF Retention)

The test substrates from the original in-vitro SPF measurements discussed above with applied formulations prepared according to Comparative Examples C1-C4 and Examples 1-6 were then each immersed in a controlled temperature water bath (30° C.) with a propeller agitation speed of 300 rpm for an hour. The substrates were then removed from the water bath and left to dry under ambient laboratory conditions for 20-30 minutes after which the in-vitro SPFs for each formulation was measured and compared to its original in-vitro SPF measurement and the 1 hour SPF retention was calculated as reported in TABLE 4. The substrates were then each immersed in the controlled temperature water bath under the noted conditions for an additional hour. The substrates were then removed from the water bath and left to dry under ambient laboratory conditions for 20-30 minutes after which the in-vitro SPFs for each formulation was measured and compared to its original in-vitro SPF measurement and the 2 hour SPF retention was calculated as reported in TABLE 4.

TABLE 4

| | in-vitro SPF Retention (%) | |
| --- | --- | --- |
| Example | 1 hour | 2 hour |
| Comp. Example C1 | 70 | 43 |
| Comp. Example C2 | 53 | 36 |
| Comp. Example C3 | 68 | 49 |
| Comp. Example C4 | 75 | 43 |

TABLE 4-continued

| | in-vitro SPF Retention (%) | |
| --- | --- | --- |
| Example | 1 hour | 2 hour |
| Example 1 | 81 | 61 |
| Example 2 | 87 | 67 |
| Example 3 | 87 | 73 |
| Example 4 | 90 | 70 |
| Example 5 | 81 | 72 |
| Example 6 | 76 | 66 |

Formulation Example G3: Generic Color Cosmetic Formulation

Color cosmetic formulations were prepared having the generic formulations according to Formulation Example G3 noted in TABLE 5. The Phase A ingredients were added to a beaker and mixed until uniform. The Phase C ingredients were combined in a separate container with mixing until uniform. The Phase D ingredients were combined in a separate container with mixing until uniform. The Phase D ingredients were then added to the beaker and mixed with the Phase A ingredients. The Phase C ingredients were then slowly added to the contents of the beaker. The Phase B polymer ingredient was then slowly added to the contents of the beaker with mixing. The Phase F deionized water ingredient was then added to the beaker. The Phase E ingredient was then added to the contents of the beaker. The beaker contents were then mixed until uniform to provide the product color cosmetic formulation.

TABLE 5

| Phase | Ingredient INCI name | Parts by weight (pbW) |
| --- | --- | --- |
| A | Lauryl PEG-10 Tris(trimethylsiloxy)silyethyl Dimeticone[1] | 5.46 |
| A | Isododecane[2] | 10.91 |
| B | Polymer to be tested (on a polymer solids basis) | 4.55 |
| C | Deionized water | 43.36 |
| C | Sodium chloride | 0.91 |
| C | Glycerin | 4.55 |
| C | Phenoxyethanol (and) Ethylhexylglycerin[3] | 0.91 |
| D | Iron Oxide (CI 77499), dimethicone[4] | 0.06 |
| D | Iron Oxide (CI 77491), dimethicone[5] | 0.23 |
| D | Iron Oxide (CI 77491), dimethicone[6] | 0.99 |
| D | Titanium Dioxide, dimethicone[7] | 5.28 |
| D | Caprylyl Methicone[8] | 2.98 |
| E | Isododecane[2] | 9.09 |
| F | Deionized water | q.s. 100 |

[1]Available from The Dow Chemical Company under the tradename Dowsil™ ES-5300.
[2]Available from Presperse under the tradename Permethyl® 99A.
[3]Available from Schulke Inc. under the tradename euxyl® PE 9010.
[4]Available from Miyoshi America under tradename SAT-B-335198.
[5]Available from Miyoshi America under tradename SAT-Y-338073.
[6]Available from Miyoshi America under tradename SAT-R-338075.
[7]Available from Miyoshi America under tradename SAT-TRI-77891.
[8]Available from The Dow Chemical Company under the tradename Dowsil™ FZ-3196.

Comparative Examples C5-C7 and Examples 7-8: Color Cosmetic Formulations

The color cosmetic formulations of Comparative Examples C5-C7 and Examples 7-8 were prepared according to Formulation Example G3 with varying test polymer as noted in TABLE 6.

TABLE 6

| Example | Polymer wt % | | |
|---|---|---|---|
| | Caprylyl Methicone[1] | Example S1 | Example S2 |
| Comp. Example C5 | 100 | 0 | 0 |
| Comp. Example C6 | 0 | 100 | 0 |
| Comp. Example C7 | 0 | 0 | 100 |
| Example 7 | 0 | 50 | 50 |
| Example 8 | 0 | 75 | 25 |

[1]Available from The Dow Chemical Company under the tradename Dowsil™ FZ-3196.

Wear Resistance

The color cosmetic formulations prepared according to Comparative Examples C5-C7 and Examples 7-8 were each coated on two separate white vinyl charts (available from Leneta) using a doctor blade film applicator with the gap set at 6 mils (0.1524 mm) and allowed to dry at 22° C. for at least 48 hours. The color reading of each sample was then measured by colorimeter (Ocean Optics). The wear resistance of the deposited film of color cosmetic formulations was characterized by the change (ΔE) before and after abrasion with a pre-cut bath towel (55 mm×45 mm). The bath towel was fixed to a moving robotic part that moves back and forth periodically at a constant speed. The film was abraded by the bath towel by 3 wear cycles under a pressure of approximately 600 Pa, each wear cycle lasts 6 seconds. Readings were taken from five point on each deposited film. The average of the five readings from each of the duplicate deposited films is provided in TABLE 7.

TABLE 7

| Color cosmetic formulation | ΔE |
|---|---|
| Comp. Example C5 | 9.8 |
| Comp. Example C6 | 4.8 |
| Comp. Example C7 | 5.2 |
| Example 7 | 2.6 |
| Example 8 | 2.5 |

We claim:

1. A color cosmetic formulation, comprising:
a color ingredient; and
a polymer blend, comprising
30 to 90 wt %, based on weight of the polymer blend, of a single stage polymer and
10 to 70 wt %, based on weight of the polymer blend, of a silicone-grafted vinyl copolymer;
wherein the single stage polymer, comprises:
90 to 99.8 wt %, based on weight of the single stage polymer, of structural units of a monoethylenically unsaturated non-ionic monomer, wherein the monoethylenically unsaturated non-ionic monomer is selected from the group consisting of a mixture of (i) 58 to 61 wt % of a C1-4 alkyl (meth)acrylate, wherein the C1-4 alkyl (meth)acrylate is a mixture of 33 to 35 wt % of methyl (meth)acrylate and 65 to 67 wt % of n-butyl (meth)acrylate; and (ii) 39 to 42 wt % of a C8-22 alkyl (meth)acrylate, wherein the C8-22 alkyl (meth)acrylate is 2-ethylhexyl acrylate;
0.19 to 10 wt %, based on weight of the single stage polymer, of structural units of a monoethylenically unsaturated carboxylic acid monomer, wherein the monoethyleneically unsaturated carboxylic acid monomer is methacrylic acid; and
0.01 to 2 wt %, based on weight of the single stage polymer, of structural units of a multiethylenically unsaturated monomer having at least two ethylenically unsaturated groups per molecule, wherein the multiethylenically unsaturated monomer having at least two ethylenically unsaturated groups per molecule is ally methacrylate (ALMA); and
wherein the silicone-grafted vinyl copolymer, comprises:
25 to 95 wt %, based on weight of the silicone-grafted vinyl copolymer, of structural units of a vinyl monomer, wherein the vinyl monomer is selected from the group consisting of methyl acrylate, ethyl acrylate, n-propyl acrylate, isopropyl acrylate, methyl methacrylate, ethyl methacrylate, n-propyl methacrylate, isopropyl methacrylate, n-butyl acrylate, isobutyl acrylate, tert-butyl acrylate, n-hexyl acrylate, cyclohexyl acrylate, 2-ethylhexyl acrylate, n-butyl methacrylate, isobutyl methacrylate, tert-butyl methacrylate, n-hexyl methacrylate, 2-ethylhexyl methacrylate, styrene and mixtures thereof; and
5 to 75 wt %, based on weight of the silicone-grafted vinyl copolymer, of structural units of a carbosiloxane dendrimer of formula (I)

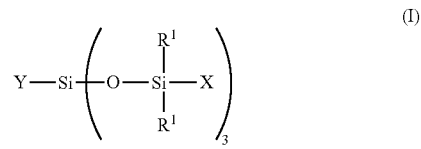

wherein each $R^1$ is a methyl group; wherein each X is a silylalkyl group of formula (II)

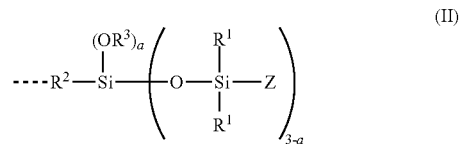

wherein $R^2$ is a C2 alkylene group; wherein each $R^3$ is independently a $C_{1-10}$ alkyl group; wherein each Z is independently selected from the group consisting of a hydrogen, a $C_{1-10}$ alkyl group, an aryl group and a silylalkyl group of formula (II);
wherein a is 0; wherein Y is selected from the group consisting of formula (III)

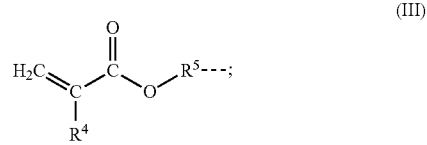

wherein each $R^4$ is a methyl group; wherein $R^5$ is a $C_3$ alkylene group.

2. The color cosmetic formulation of claim 1, wherein the vinyl monomer includes methyl methacrylate and butyl acrylate.

3. The color cosmetic formulation of claim 2, wherein the color ingredient is selected from the group consisting of inorganic pigments, organic pigments, aqueous pigment dispersions and mixtures thereof.

4. The color cosmetic formulation of claim 3, wherein the color ingredient is selected from the group consisting of Ext. D&C Yellow No. 2, Ext. D & C Violet No. 2, FD&C Red No. 4, FD&C Red No. 40, FD&C Yellow No. 5, FD&C Yellow No. 6, FD&C Green No. 3, FD&C Blue No. 1, D&C Yellow No. 7, D&C Yellow No. 8, D&C Yellow No. 10, D&C Yellow No. 11, D&C Violet No. 2, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 34, D&C Red No. 33, D&C Red No. 36, D&C Green No. 5, D&C Green No. 6, D&C Green No. 8, D&C Blue No. 4, D&C Orange No. 4, D&C Orange No. 5, D&C Orange No. 10, D&C Orange No. 11, D&C Brown No. 1, Aluminum powder, Annatto, Bismuth citrate, Bismuth Oxychloride, Bronze powder, Caramel, Carmine, β-Carotene, Chromium hydroxide green, Chromium oxide green, Copper chlorophyllin, Copper powder, Dihydroxyacetone, Ferric Ammonium ferrocyanide, Ferric ferrocyanide, Guanine, Iron oxide, Manganese Violet, Mica, Silver, Titanium Dioxide, Ultramarine, Zinc Oxide and mixtures thereof.

5. The color cosmetic formulation of claim 4, wherein the color ingredient includes at least one iron oxides.

6. The color cosmetic formulation of claim 5, further comprising a suncare active.

7. The color cosmetic formulation of claim 6, further comprising a dermatologically acceptable carrier and wherein the color cosmetic formulation has a pH of 5.5 to 7.5.

8. The color cosmetic formulation of claim 1, wherein the polymer blend comprises:
    50 to 80 wt %, based on weight solids of the polymer blend, of the single stage polymer, and
    20 to 50 wt %, based on weight solids of the polymer blend, of the silicone-grafted vinyl copolymer.

9. The color cosmetic formulation of claim 1, wherein the polymer blend comprises:
    60 to 70 wt %, based on weight solids of the polymer blend, of the single stage polymer, and
    30 to 40 wt %, based on weight solids of the polymer blend, of the silicone-grafted vinyl copolymer.

10. The color cosmetic formulation of claim 1, wherein the weight ratio of the single stage polymer to the silicone-grafted vinyl copolymer is 3:1 to 1:2.

11. The color cosmetic formulation of claim 1, wherein the weight ratio of the single stage polymer to the silicone-grafted vinyl copolymer is 3:1 to 1:1.

12. The color cosmetic formulation of claim 7 wherein the dermatologically acceptable carrier is water.

* * * * *